United States Patent
Macret et al.

(10) Patent No.: US 9,024,081 B2
(45) Date of Patent: May 5, 2015

(54) PURIFICATION OF CRUDE GLYCEROL

(75) Inventors: Richard Macret, Sao Paulo (BR); Celio Ferraz Wagner Lourenco, Sao Paulo (BR)

(73) Assignee: Rhodia Poliamida e Especialidades LTDA, Sao Paulo (BR)

( * ) Notice: Subject to any disclaimer, the term of this patent is extended or adjusted under 35 U.S.C. 154(b) by 592 days.

(21) Appl. No.: 12/993,137

(22) PCT Filed: May 18, 2009

(86) PCT No.: PCT/IB2009/005635
§ 371 (c)(1),
(2), (4) Date: Jan. 27, 2011

(87) PCT Pub. No.: WO2009/141702
PCT Pub. Date: Nov. 26, 2009

(65) Prior Publication Data
US 2011/0112336 A1    May 12, 2011

(30) Foreign Application Priority Data
May 19, 2008 (FR) .................. 08 02689

(51) Int. Cl.
C07C 29/74 (2006.01)
C07C 29/92 (2006.01)

(52) U.S. Cl.
CPC ..................... *C07C 29/92* (2013.01)

(58) Field of Classification Search
CPC ....................................... C07C 29/92
USPC ........................................... 568/869
See application file for complete search history.

(56) References Cited

U.S. PATENT DOCUMENTS
2010/0099894 A1    4/2010    Dubois et al.

FOREIGN PATENT DOCUMENTS
FR    2906807 A1    4/2008
GB    933714        8/1963
WO    WO 97/01523 A1    1/1997

OTHER PUBLICATIONS
International Search Report corresponding to PCT/IB 2009/005635, Jul. 2009.

*Primary Examiner* — Rosalynd Keys
(74) *Attorney, Agent, or Firm* — Dentons US LLP

(57) ABSTRACT

Crude glycerol obtained from raw materials, such as the glycerol obtained during the production of biodiesel or glycerol obtained during the conversion of fats or oils, is purified by forming a dioxolane therefrom by reacting the crude glycerol with a ketone or aldehyde, separating the dioxolane thus formed, converting the dioxolane into purified glycerol and ketone/aldehyde, and recovering the glycerol thus purified.

18 Claims, No Drawings

PURIFICATION OF CRUDE GLYCEROL

CROSS-REFERENCE TO PRIOR-EARLIER APPLICATIONS

This application is the U.S. National Stage of PCT/IB 2009/005635, filed May 18, 2009 and designating the United States (published in the French language on Nov. 26, 2009, as WO 2009/141702 A1; the title and abstract were also published in English), which claims priority under 35 U.S.C. §119 of FR 0802689, filed May 19, 2008, each hereby expressly incorporated by reference in its entirety and each assigned to the assignee hereof.

The present invention relates to a process for the purification of the crude glycerol obtained from starting materials such as the glycerol obtained during the manufacture of biodiesel or the glycerol obtained during the conversion of fats or oils. The invention is targeted in particular at reacting the crude product comprising glycerol with specific organic compounds of acetone and aldehyde type.

PRIOR ART

Glycerol, 1,2,3-propanetriol, is present in the combined form in plant and animal oils and fats. It is in particular present in the form of triglycerides combined with fatty acids, such as stearic acid, oleic acid, palmitic acid and lauric acid. The most widespread industrial process for obtaining glycerol from plant and animal oils and fats involves saponification reactions, high pressure hydrolysis reactions and transesterification reactions with alcohols, such as ethanol or methanol.

Glycerol is also a byproduct from biodiesel which is obtained generally by the transesterification of glycerides with short-chain alcohols, for example methanol or ethanol.

The transesterification reaction is catalyzed by an acid or a base, according to the characteristics of the oils and/or fats used. After the transesterification reaction, the resulting esters are separated from the excess reactants, from the catalyst and from the byproducts by a process comprising two stages. First, the glycerol is separated by settling or centrifuging and then the soaps, the catalyst residues and alcohol residues are removed by washing with water and sparging or use of magnesium silicate with filtration. The extensive production of biodiesel as alternative to fossil sources is accompanied by high production of glycerol obtained as byproduct.

Depending on the manufacturing processes, the crude glycerol obtained comprises impurities which involve numerous and complex treatment stages.

To this end, it is known in particular to purify the crude glycerol by distillation, the operation being carried out with specific conditions in order not to detrimentally affect the glycerol, which decomposes at temperatures of 170-180° C. and which can polymerize and generate impurities. Such a purification process is therefore not advantageous industrially.

There thus exists a number of complex techniques which have been developed in the past in order to purify glycerol while avoiding decompositions or other undesirable reactions.

For example, patent U.S. Pat. No. 4,655,879 describes a very laborious process for the purification of crude glycerol which involves a large number of stages in which the crude glycerol is first basified in the presence of air for oxidation and then distilled at high temperatures under reduced pressures. As the glycerol obtained exhibits an undesirable color, it is furthermore necessary to carry out an additional treatment with activated charcoal.

Patent U.S. Pat. No. 4,990,695 describes the purification of crude glycerol with a combination of operations, such as the adjustment of the pH within a range from 9 to 12, heating the medium at 100° C., microfiltration and subsequent ultrafiltration. The glycerol obtained is then distilled, optionally after a treatment with ion-exchange compounds.

The development is thus desired of a simple and industrial process for the purification of glycerol from crude glycerol which is relatively inexpensive and which takes place under ordinary temperature and pressure conditions and which makes it possible to obtain purified glycerol having a quality appropriate for a certain number of applications, while avoiding the abovementioned disadvantages.

INVENTION

It has now been demonstrated that it is possible to purify crude glycerol by a process which is simple to carry out, which is efficient and which furthermore does not detrimentally affect the glycerol or its color. This process consists in generating a dioxolane by reaction of the crude glycerol and of ketone or of aldehyde and in purifying said dioxolane by distillation in order to subsequently reconvert it to glycerol and to ketone or aldehyde.

There are numerous advantages to such a process. Specifically, this process makes possible excellent purification and separation of the glycerol, whatever the type of crude glycerol used in terms of impurities and pH. Furthermore, the intermediate dioxolane formed exhibits a lower boiling point than glycerol, making it possible to carry out a distillation under ordinary, industrial and economic conditions without bringing about decomposition of the glycerol. Another advantage lies in the fact that the dioxolane does not comprise free hydroxyl groups, in contrast to glycerol, which makes it possible to prevent side reactions and polymerization reactions of the glycerol, in particular during the distillation.

The present invention relates to a process for the purification of crude glycerol comprising at least the following stages:
(a) formation of a dioxolane by reaction between the crude glycerol and a ketone or an aldehyde;
(b) separation by distillation of the dioxolane formed;
(c) reversion of the dioxolane to form glycerol and ketone or aldehyde;
(d) recovery of the glycerol.

The process of the invention can be carried out continuously or batchwise. The stages mentioned can be carried out successively and in or not in succession to one another. Each of the stages of the process can be carried out continuously or batchwise.

The crude glycerol is preferably obtained from renewable starting materials; in particular, the crude glycerol is obtained during the manufacture of biodiesel or is obtained during conversions of fats or oils, particularly animal or vegetable fats or oils. The crude glycerol is generally obtained by a saponification, transesterification and/or hydrolysis reaction on animal or vegetable fats or oils.

The crude glycerol generally comprises from 5 to 95% by weight of glycerol, in particular from 40 to 90% by weight of glycerol. The crude glycerol also comprises inorganic salts, glycerides, water and other organic compounds.

The crude glycerol can optionally be treated for the process of the invention, in particular, for example, by adjustment of the pH, filtration or distillation.

It is thus possible to filter the crude glycerol in order to remove insoluble organic materials and/or to distil it, generally at temperatures of between 100 and 120° C. at atmospheric pressure, in order to remove water and volatile compounds.

Stage a) of the process according to the invention is targeted at forming a dioxolane by reaction of the glycerol present in the crude glycerol and of a ketone or of an aldehyde.

The dioxolane according to the invention can be an acetal or a ketal. Acetals are obtained by nucleophilic addition of an alcohol to an aldehyde in an acidic medium, followed by removal of water. Ketals are obtained by the same type of reaction carried out on ketones.

The ketones preferably used are acetone, cyclohexanone, methylcyclohexanone, cyclopentanone, methylcyclopentanone and methyl isobutyl ketone, 4-hydroxy-4-methyl-2-pentanone, 2-butanone, 3-butanone, 4-methyl-3-penten-2-one, 2-nonanone, 2-pentanone and 3-methyl-2-butanone.

The aldehydes preferably used are formaldehyde, acetaldehyde and furfuraldehyde.

It is possible in particular to use, according to the invention, one or more ketones and/or aldehydes in order to react with the glycerol in the reaction medium.

Depending on the process used, it is possible to use various proportions of glycerol and of ketone or of aldehyde in the reaction medium. For example, in the batchwise process, it is possible to use a molar ratio of 1 to 5 of ketone or of aldehyde with respect to the glycerol. In a continuous process, it is possible, for example, to use glycerol in a loop and to add small proportions of ketone or of aldehyde, in particular from 5 to 20 mol %.

The ketal or acetal formed is a compound of 1,3-dioxolane type corresponding in particular to the following general formula (I):

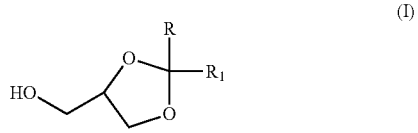

in which R and $R_1$ represent, independently of one another, a hydrogen atom or an alkyl chain comprising from 1 to 10 carbon atoms, in particular from 1 to 5 carbon atoms, such as in particular the methyl, ethyl, propyl, isopropyl, butyl, isobutyl, pentyl and isopentyl groups.

In the case of a reaction with an aldehyde, one of the groups R or $R_1$ is a hydrogen atom. In the case of a reaction with a ketone, the groups R and $R_1$ do not represent a hydrogen atom.

Preference is given in particular to 2,2-dimethyl-1,3-dioxolane-4-methanol and 2-isobutyl-2-methyl-1,3-dioxolane-4-methanol.

The ketal or acetal formed preferably exhibits a good solubility in water, in particular greater than 20 000 mg/kg at ambient temperature. The ketones and aldehydes used may also exhibit a solubility of greater than 20 000 mg/kg at ambient temperature.

The reaction for the formation of the dioxolane is generally carried out at a temperature of between 50 and 150° C., preferably between 60 and 80° C.

This reaction can be carried out in the absence or presence of solvent.

This reaction can be carried out for from 2 to 8 hours, generally between 3 and 6 hours.

This reaction is preferably carried out in an acidic medium, in particular with a pH varying from 2.5 to 7.0, preferably from 5.0 to 7.0, most preferably from 5.5 to 7.0.

It is possible in particular to use acid catalysts for this reaction, such as organic or inorganic acids or their salts. Mention may be made of the use of acetic acid, sulfuric acid or ion-exchange resins of carboxylic or sulfonic type. These resins can be present on a fixed bed in the reactor.

At the end of the reaction, it is possible to neutralize the catalyst, in particular by addition of sodium carbonate or sodium hydroxide.

The unreacted aldehyde and ketone can be removed by simple distillation.

Such a reaction between glycerol and a ketone or an aldehyde to form a dioxolane is well known and is mentioned in particular in the following publications: R. J. Fessenden & J. F. Fessenden, Organic Chemistry, second edition, page 524, 1982, and T. W. Greene, Protective Groups in Organic Chemistry, John Wiley & sons, 1981.

Stage b) is targeted at the separation of the dioxolane formed from the reaction medium by distillation, preferably under reduced pressure.

Use may be made of one or more distillation columns in carrying out the distillation. It is possible in particular to distil the various compounds on the same distillation column by varying the temperature and optionally the pressure; for example to distil the ketone or the aldehyde, then an increase in the temperature in order to distil the water and then again an increase in the temperature in order to distil the dioxolane formed.

Use is usually made of temperatures between 60 and 190° C. and pressures between 2 and 1000 mbar.

The dioxolane obtained generally exhibits a purity of between 97 and 99% and can comprise small amounts of salts, of glycerides and/or of esters of fatty acids.

Stage c) is targeted at the reaction for the reversion of the dioxolane to give glycerol and ketone or aldehyde, in particular by acid catalysis in the presence of water.

This reaction can be carried out continuously or batchwise. The reaction can in particular be a homogeneous or heterogeneous catalysis.

The catalysts used for this reaction can be organic or inorganic acids or their salts. Mention may in particular be made of the use of acetic acid, of sulfuric acid or ion-exchange resins of carboxylic or sulfonic type. These resins can be present on a fixed bed in the reactor.

Use is generally made of 0.5 to 1.0% by weight, preferably of 0.5 to 0.7% by weight, of catalyst, with respect to the weight of the reaction mass.

The temperature of the reversion reaction can be between 25 and 150° C., depending on the aldehyde or the ketone used.

The aldehydes and ketones can be recovered by distillation, in particular under reduced pressure, optionally under nitrogen.

The purified glycerol obtained according to the invention exhibits in particular a purity of between 95 and 99.5%.

A specific language is used in the description so as to facilitate the understanding of the principle of the invention. Nevertheless, it should be understood that no limitation on the scope of the invention is envisaged by the use of this specific language. Modifications and improvements can in particular be envisaged by a person conversant with the technical field concerned on the basis of his own general knowledge.

The term "and/or" includes the meanings "and", "or" and all the other possible combinations of the elements connected to this term.

Other details or advantages of the invention will become more clearly apparent in the light of the examples given below solely by way of indication.

EXPERIMENTAL PART

Example 1

1000 g of crude product obtained by a transesterification reaction on soybean oil, comprising 85% by weight of glycerol, 6% by weight of water and also glycerides, salts and other impurities and having a pH of 5.5-6.0 (in a 10% by weight aqueous solution), are filtered in order to remove small amounts of suspended fatty substances.

2145 g of acetone are added and the reaction medium is heated at reflux at a temperature of 65° C. for 4 hours and then cooled at ambient temperature and neutralized by addition of an aqueous sodium carbonate solution.

The excess acetone is recovered by distillation at a temperature of 60-70° C. at atmospheric pressure and recycled without treatment. The water formed during the reaction is distilled at a temperature of 100-120° C. at atmospheric pressure. The 2,2-dimethyl-1,3-dioxolane-4-methanol is recovered by distillation at a temperature of 190° C. at atmospheric pressure.

An analysis by gas chromatography reveals a 2,2-dimethyl-1,3-dioxolane-4-methanol purity of greater than 98%.

Example 2

A similar experiment to that of example 1 is carried out using this time 2 kg of crude product comprising 42% by weight of glycerol, 14% by weight of water and a large amount of volatile products (methanol, ethanol). The acetone is used in the same molar ratio as is for example 1 and the 2,2-dimethyl-1,3-dioxolane-4-methanol obtained has a purity of 98%.

Example 3

3.5 kg of crude glycerol in the paste form at a temperature of 25° C. obtained by a transesterification reaction on animal fats and on methanol, comprising 80% by weight of glycerol, glycerides and inorganic salts and having a pH of 11.7 (in a 10% by weight aqueous solution), is heated at a temperature of 60-70° C. in order to obtain a viscous liquid. An aqueous solution comprising 50% by weight of sulfuric acid (422.3 g) is added to the medium in order to obtain a pH of 3.0. The free fatty acids and other impurities are separated by filtration (541.2 g) and a liquid solution (3335.4 g) is obtained.

A reaction with acetone is then carried out under conditions similar to those of example 1 and 2,2-dimethyl-1,3-dioxolane-4-methanol is obtained with a purity of 97.5%.

Example 4

3.5 kg of crude product similar to that of example 1 are heated at a temperature of 100° C. under a pressure of 100 mmHg in order to reduce the content of water and of volatile compounds.

12.9 kg of MIBK (methyl isobutyl ketone) are then added and the reaction medium is heated at reflux at a temperature of 110° C. for 5 hours while continually supplying MIBK and while removing water. The reaction medium is then cooled to ambient temperature and a portion of the excess MIBK is separated by settling. The reaction mass is neutralized with an aqueous sodium hydroxide solution.

The excess MIBK is removed by distillation at a temperature of 110-140° C. and at atmospheric pressure, followed by distillation of the medium at a temperature of 160° C. and a pressure of 200 mmHg, making it possible to obtain 2-isobutyl-2-methyl-1,3-dioxolane-4-methanol with a purity of 98%.

Example 5

16 kg of 2,2-dimethyl-1,3-dioxolane-4-methanol, 3.2 kg of water and 4.8 g of 98% sulfuric acid are added to a 27-liter reactor. The medium is mixed at ambient temperature for 1 hour. An analysis of the water shows that, after 1 hour, 50 to 55% by weight of the 2,2-dimethyl-1,3-dioxolane-4-methanol has been converted to glycerol and acetone. The acetone formed is removed from the medium by distillation at a temperature of 160° C. and a pressure of 100 mmHg.

The glycerol obtained is clear and exhibits a purity of 98%.

Example 6

7 kg of 2-isobutyl-2-methyl-1,3-dioxolane-4-methanol, 0.5 kg of water and 1.5 g of 98% sulfuric acid are added to a 10-liter reactor. The medium is mixed at ambient temperature for 1.5 hours. An analysis of the water shows that, after 1 hour, 45 to 50% by weight of the 2-isobutyl-2-methyl-1,3-dioxolane-4-methanol has been converted to glycerol and MIBK. The MIBK formed is removed from the medium by distillation at a temperature of 160° C. and a pressure of 200 mmHg.

After complete removal of the MIBK from the medium, the excess water is distilled off at a temperature of 100° C. and a pressure of 100 mmHg.

The glycerol obtained is clear and exhibits a purity of 95%.

What is claimed is:

1. A process for the purification of crude glycerol consisting essentially of carrying out the following stages successively and in succession to one another:
    (a) forming a dioxolane by reacting the crude glycerol with a ketone or an aldehyde, wherein the crude glycerol comprises 40% to 90% by weight glycerol and wherein the dioxolane has a solubility in water of greater than 20,000 mg/kg at ambient temperature;
    (b) separating, by distillation, the dioxolane thus formed;
    (C) reverting the dioxolane into purified glycerol and ketone or aldehyde; and
    (d) recovering the glycerol thus purified.

2. The process as defined by claim 1, wherein the crude glycerol originates from renewable starting materials.

3. The process as defined by claim 1, wherein the crude glycerol is obtained during the manufacture of biodiesel or during the conversion of fats or oils.

4. The process as defined by claim 1, wherein the ketone is selected from the group consisting of acetone, cyclohexanone, methylcyclohexanone, cyclopentanone, methylcyclopentanone and methyl isobutyl ketone, 4-hydroxy-4-methyl-2-pentanone, 2-butanone, 3-butanone, 4-methyl-3-penten-2-one, 2-nonanone, 2-pentanone and 3-methyl-2-butanone.

5. The process as defined by claim 1, wherein the aldehyde is selected from the group consisting of formaldehyde, acetaldehyde and furfuraldehyde.

6. The process as defined by claim 1, wherein the dioxolane has the following general formula (I):

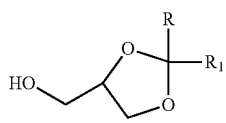 (I)

in which R and R₁, which may be identical or different, are each a hydrogen atom or an alkyl radical having from 1 to 10 carbon atoms.

7. The process as defined by claim 1, wherein the reaction of stage (a) comprises a nucleophilic addition in an acidic medium.

8. The process as defined by claim 1, wherein the reaction medium of stage (a) comprises an acid catalyst.

9. The process as defined by claim 1, wherein the reaction medium of stage (a) comprises an acid catalyst selected from the group consisting of acetic acid, sulfuric acid and carboxylic or sulfonic ion-exchange resins.

10. The process as defined by claim 1, wherein the distillation of stage (b) is carried out under reduced pressure.

11. The process as defined by claim 1, wherein the distillation of stage (b) is carried out at a temperature ranging from 60 to 190°C.

12. The process as defined by claim 1, wherein the reversion of stage (c) comprises an acid catalysis carried out in the presence of water.

13. The process as defined by claim 1, wherein the reversion medium of stage (c) comprises an acid catalyst.

14. The process as defined by claim 1, wherein the reversion medium of stage (c) comprises an acid catalyst selected from the group consisting of acetic acid, sulfuric acid and carboxylic or sulfonic ion-exchange resins.

15. The process as defined by claim 1 said crude glycerol emanating from the production of biodiesel or from the conversion of fats or oils.

16. The process of claim 6, wherein the dioxolane has formula (I) in which R and R₁, which may be identical or different, are each an alkyl radical having from 1 to 5 carbon atoms.

17. A process for the purification of crude glycerol consisting essentially of carrying out the following stages successively and in succession to one another:

(a) forming a dioxolane having formula (I)

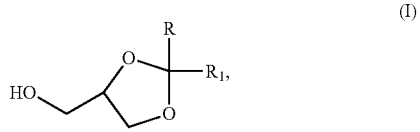 (I)

in which R and R₁, which may be identical or different, are each a hydrogen atom or an alkyl radical having from 1 to 10 carbon atoms, by reacting the crude glycerol with a ketone or an aldehyde, wherein the crude glycerol comprises 40% to 90% by weight glycerol and wherein the dioxolane has a solubility in water of greater than 20,000 mg/kg at ambient temperature;

(b) separating, by distillation, the dioxolane thus formed;

(c) reverting the dioxolane into purified glycerol and ketone or aldehyde; and (d) recovering the glycerol thus purified.

18. The process of claim 17, wherein the dioxolane has formula (I), in which R and R₁, which may be identical or different, are each an alkyl radical having from 1 to 5 carbon atoms.

* * * * *